United States Patent
Russell et al.

(10) Patent No.: US 7,285,203 B2
(45) Date of Patent: Oct. 23, 2007

(54) METHOD AND APPARATUS FOR INSTRUMENTAL ANALYSIS IN REMOTE LOCATIONS

(76) Inventors: Gordon I. Russell, 442 Indian Road, Burlington, Ontario (CA) L7S 3T3; Murray D. Stenekes, 205 Parkview Drive, Hamilton, Ontario (CA) L8S 3Y4

( * ) Notice: Subject to any disclaimer, the term of this patent is extended or adjusted under 35 U.S.C. 154(b) by 445 days.

(21) Appl. No.: 10/617,211

(22) Filed: Jul. 11, 2003

(65) Prior Publication Data

US 2005/0006250 A1    Jan. 13, 2005

(51) Int. Cl.
*C23F 13/00*    (2006.01)

(52) U.S. Cl. .................. 205/725; 205/724; 205/726; 205/727; 205/775.5; 205/776; 205/777

(58) Field of Classification Search ................ 205/724, 205/725, 726, 727, 775.5, 776, 776.5, 777
See application file for complete search history.

(56) References Cited

U.S. PATENT DOCUMENTS

| | | | |
|---|---|---|---|
| 2,329,961 A | 9/1943 | Walker | 204/196 |
| 2,480,089 A | 8/1949 | Slocombe | 260/453 |
| 2,941,935 A | 6/1960 | Miller et al. | 204/196 |
| 3,001,919 A | 9/1961 | Petrocokino | 204/148 |
| 3,272,731 A | 9/1966 | Hutchison et al. | 204/195 |
| 3,461,051 A | 8/1969 | Vrable | 204/147 |
| 3,595,774 A | 7/1971 | Bremerman | 204/196 |
| 3,729,773 A | 5/1973 | Dillon | 17/11 |

(Continued)

OTHER PUBLICATIONS

Landrum, Fundamentals of Designing for Corrosion Control, 1989, pp. 46-53, 102-107, no month available.

(Continued)

*Primary Examiner*—Bruce F. Bell
(74) *Attorney, Agent, or Firm*—Mark W. Sajewycz

(57) ABSTRACT

The present invention provides a method and apparatus for instrumental analysis in remote locations. In one embodiment, the present invention provides a method of controlling cathodic protection being applied to a metal structure having a surface disposed in an electrolytic environment comprising electrically connecting a metal coupon to the surface of the metal structure, positioning the metal coupon at a predetermined position relative to the surface of the metal structure and within the electrolytic environment, applying a cathodic protection agent to the surface of the metal structure to effect cathodic protection of the surface of the metal structure, measuring a cathodic protection indication proximate to the metal coupon, comparing the cathodic protection indication with a predetermined value, and adjusting the cathodic protection agent being applied to the surface of the metal structure in response to the comparison. In this respect, the present invention provides a system for controlling the efficacy of cathodic protection being applied to a metal structure disposed in an electrolytic environment comprising an electrical vintage and current source of applying an electrical current to the metal structure to effect cathodic protection of the metal structure, a measurement apparatus for measuring the efficacy of the cathodic protection, the measurement apparatus being electrically connected to the metal structure, and a passage for receiving movement of the means for measuring to effect positioning of the measurement apparatus at a predetermined position relative to the metal structure. The passage of the present invention could also be used to facilitate non-destructive testing at remote locations, as well as to mitigate or prevent stray current discharge.

29 Claims, 9 Drawing Sheets

U.S. PATENT DOCUMENTS

| | | | | |
|---|---|---|---|---|
| 3,831,389 | A | 8/1974 | Lipona | 62/63 |
| 3,861,935 | A | 1/1975 | Ohnemuller et al. | 106/306 |
| 4,435,261 | A | 3/1984 | Mintz et al. | 204/168 |
| 4,623,435 | A | 11/1986 | Nebgen et al. | 204/148 |
| 4,654,217 | A | 3/1987 | Nagoshi | 426/524 |
| 4,689,963 | A | 9/1987 | Sakai | 62/64 |
| 4,755,267 | A | 7/1988 | Saunders | 204/147 |
| 4,968,520 | A | 11/1990 | Wang | 426/524 |
| 5,165,256 | A | 11/1992 | Yamada | 62/373 |
| 5,168,712 | A | 12/1992 | Coelho et al. | 62/64 |
| 5,295,368 | A | 3/1994 | Franklin | 62/307 |
| 5,538,535 | A | 7/1996 | Pinnau et al. | 95/41 |
| 6,004,607 | A | 12/1999 | Brackebusch et al. | 426/524 |
| 6,238,530 | B1 | 5/2001 | Yodhida et al. | 204/252 |
| 6,744,265 | B2 * | 6/2004 | Yunovich et al. | 324/700 |

OTHER PUBLICATIONS

Laboratory Product News, Oct. 2000, pp. 16-18.

Uhlig, Alloying for Corrosion Resistance, Stainless Steels, Chapter 18, 1985, pp. 312-317, no month available.

France Jr., Crevice Corrosion of Metals, Localized Corrosion—Cause of Metal Failure, 1972, pp. 164-197, no month available.

Russell, Stenekes, Targeting Cathodic Preservation of Pipeline Integrity, NACE International Northern Area International Conference, Nov. 2000.

Verink Jr., Evaluation of the Tendency of Dealloying in Metal Systems, Localized Corrosion—Cause of Metal Failure, 1972, pp. 308-309, no month available.

Sklarska-Smialowska, Measurement of the Susceptibility of Pitting, Chapter 3, pp. 39-65; Sites of Pit Nucleation, Chapter 4, pp. 69-97; Kinetics of Pit Growth, Chapter 6, p. 124; Pit Morphology in Various Steels and Aluminum Alloys, Chapter 7, p. 133; Effects of Environmental Factors on Pitting, Chapter 9, p. 221; Pitting at Cathodic Potentials, Chapter 15, p. 339); Composition of the Electrolyte Contained in Pits, Chapter 18, pp. 351-373; Theories of Pitting Corrosion, Chapter 19, p. 382—Pitting Corrosion of Metals, 1986, no month available.

Wilhelm, Galvanic Corrosion Caused by Corrosion Products, Galvanic Corrosion, 1988, pp. 24-25, no month available.

Al Zaharani, Todd, Oldfield, Bimetallic Joints in Multistage Flash Desalination Plants, Galvanic Corrosion, 1988, p. 329, no month available.

Shutze, Healing of Oxide Scale Damage (Chapter 7), Estimation of the Critical Strain Rate for Crack Healing (Chapter 7.3), Protective Oxide Scales and Their Breakdown, 1997, p. 122, no month available.

Abdulsalam, M.I., Shinohara, T., Technical Note: Crevice Corrosion of Stainless Steel in Hot Salt Water, Jan. 2003.

Toyoji Kobayashi, "Effect of Environmental Factors on the Protective Potential of Steel", Proceedings of the Fifth International Congress on Metallic Corrosion, May 1972, pp. 627-630, published by National Association of Corrosion Engineers, Texas, U.S.A., Library of Congress No. 74-25184.

J.M. Morgan, "Cathodic Protection", National Association of Corrosion Engineers (NACE) 1987 2nd Edition, Chapter 1 - pp. 34 to 48, Chapter 2 - pp. 59 to 62, Chapter 3 - pp. 68 to 70, Chapter 4 - pp. 119 to 125, Chapter 5 - pp. 146 to 147 and pp. 175 to 181, Chapter 6 - pp. 193 to 196, 200, 205, and 217, Chapter 10 - p. 483. (Appendix A).

Johnson, M.J. "Relative Critical Potential for Pitting Corrsosion of Some Stainless Steels", pp. 262 to 265 of "Localized Corrosion Cause of Metal Failure" ASTM Publications, Library of Congress Catalogue Card No. 72-86243, 1972 (Appendix B).

Bond, A.P. "Pitting Corrosion - A Review of Recent Advances in Testing Methods and Interpretation" pp. 254 to 261, in "Localized Corrosion - Cause of Metal Failure", ASTM Publications, Library of Congress Catalogue Card No. 72-86243, 1972 (Appendix C).

Morgan, John "Cathodic Protection", 2nd edition, Nale. 1987, pp. 228-229, Library of Congress 87-061750 ISBN 0-915567-28-8 (Appendix E).

Patent Abstract of Japan vol. 012, No. 128 (c-489), Apr. 20, 1988 & JP 62 247088 A, Matsushita Electric Ind Co. Ltd., Oct. 28, 1987.

Tomashov et al., "Electrochemical Protection of Buried Structures From Stray Current Corrosion By Means of Unilaterally Polarising Anodes", in Tomashov, N D, "Theory of Corrosion and Protection of Metals", 1966, pp. 68-69, The Macmillan Company, 60th Fifth Avenue, New York 10011.

* cited by examiner

METHOD AND APPARATUS FOR INSTRUMENTAL ANALYSIS IN REMOTE LOCATIONS

FIELD OF THE INVENTION

The present invention relates to a method and apparatus for measuring and controlling the efficacy of cathodic protection, and more particular it relates to a method and apparatus for measuring and controlling parameters and/or to improve the efficacy of cathodic protection at a metal surface disposed in a remote location where visual inspection of the metal structure is rendered difficult.

BACKGROUND OF THE INVENTION

Metal structures immersed in aqueous electrolytic environments are susceptible to corrosion. Corrosion occurs when the current discharges from the metal surface into the electrolyte, thereby creating anodic areas. Cathodic protection is applied to the metal structure with a view to forcing the entire structure surface exposed to the electrolyte to collect protective current. When this environmental condition has been attained, the structure's entire exposed surface becomes cathodic, and corrosion may be sufficiently mitigated, controlled, or prevented. The structure's surface can be made a cathode by means of an externally impressed direct current and/or an attachment to sacrificial anodes. The effectiveness of such cathodic protection can be assessed by measuring the potential of the structure relative to a reference electrode. However, such measurements do not provide an accurate indication of the degree of cathodic protection in a remote or concealed area, such as within a crevice.

The term cathodic protection refers to a process whereby polarized alkaline film at the metal surface is produced by a current density. The quality of this film can be determined by, for instance, measuring it pH value, capacitance, conductance, and polarized potential across the film. However, the protective current density maintaining the polarized surface alkalinity varies significantly with kinetic stress and energy including, temperature, pressure, and motion. The efficacy of the process is determined by the current density requited to maintain the polarized level of protection, and/or the rate of depolarization upon current interruption. When the entire immersed surface becomes equally polarized a potential more negative than −620 mV to the standard hydrogen reference electrode and to the extent that a uniform film (of a thickness in angstroms) with an alkalinity of pH value of about 11.5+/−0.5 is produced, corrosion may then be prevented. Measurements of the structure's polarized surface potential are only conventionally obtained at a considerable distance from the structure. Such remotely measured potentials are, however, only indicative of the average polarized potential over a significant area. Further, such measurements of polarized potential are only a secondary indicator of the alkalinity of the protective film which is the primary means to prevent corrosion and, therefore of the efficacy of cathodic protection. Conventional auto-potential control of impressed current sources alone, therefore, is insufficient unless complemented by pH control compensating for kinetic affects such as temperature and unless the potential pH values are sufficient to stifle microbiologically influenced corrosion (MIC).

SUMMARY OF THE INVENTION

In a broad aspect, the present invention provides a method of controlling cathodic protection being applied to a metal structure having a surface disposed in an electrolytic environment comprising electrically connecting a metal coupon to the surface of the metal structure, positioning the metal coupon at a predetermined position relative to the surface of the metal structure and within the electrolytic environment, applying a cathodic protection agent to the surface of the metal structure to effect cathodic protection of the surface of the metal structure, measuring a cathodic protection indication proximate to the metal coupon, comparing the cathodic protection indication with a predetermined value, and adjusting the cathodic protection agent being applied to the surface of the metal structure in response to the comparison.

For example, the cathodic protection agent can be an electric current or a chemical composition. In one aspect, the chemical composition has a tendency to effect alkaline conditions at the surface of the metal structure.

In another aspect, the predetermined position is in close proximity to the metal structure.

In another aspect, the electrolytic environment is selected from the group consisting of: a subsurface soil environment and an aqueous solution.

In a further broad aspect, the present invention provides a system for controlling the efficacy of cathodic protection being applied to a metal structure disposed in an electrolytic environment comprising means of applying an electric current to the metal structure to effect cathodic protection of the metal structure, means for measuring the efficacy of the cathodic protection, said means for measuring being electrically connected to the metal structure, and a passage for receiving movement of the means for measuring to effect positioning of the means for measuring at a predetermined position relative to the metal structure.

In on aspect, the means for measuring the efficacy of the cathodic protection includes a means for stimulating the cathodic protection of a crevice of the metal structure.

In yet another aspect, the means for measuring the efficacy of the cathodic protection further includes a means for sensing a cathodic protection indication of the means for simulating.

In a further aspect, the means for simulating comprises a metal coupon.

In yet a further aspect, a metal coupon defines a simulated crevice.

In another aspect, the metal coupon includes first and second opposing flanges joined by a web, such that the simulated crevice is defined by the space between the first and second flanges.

In a further aspect, the coupon is electrically coupled to the metal structure.

In a further aspect, the means for sensing senses the cathodic protection indication in the crevice.

In another broad aspect, the present invention provides a system for effecting non-destructive testing of a characteristic of a target disposed in an electrolytic environment comprising means for effecting the non-destructive testing including a radiation transmitter for irradiating the target, and a receiver for receiving a response from the target to the radiation, and a passage for receiving movement of the receiver to effect positioning of the receiver at a predetermined location relative to the target.

In one aspect, the target is a metal structure having a surface disposed in an environment which is not conveniently accessible, or a metal structure having a surface submerged in an aqueous electrolytic environment, or a metal structure having a surface submerged in an electrolytic soil environment, or a metal structure having a surface submerged in an aqueous solution.

In a further broad aspect, the present invention provides a system for measuring a characteristic of a metallic structure disposed in an electrolytic environment comprising means for sensing the characteristic of the metal structure, and a passage for receiving movement of the means for sensing to effect positioning of the means for sensing at a predetermined position relative to the metal structure.

In one aspect, the means for sensing senses an electric potential of the metal structure.

In yet another broad aspect, the present invention provides a system for mitigating stray current discharging to or being discharged from a metal structure disposed in an electrolytic environment comprising: a means for predetermining a location of stray current discharge, a means for mitigating stray current discharge, and a passage for receiving movement of the means for mitigating to effect positioning of the means for mitigating at the predetermined location.

BRIEF DESCRIPTION OF THE DRAWINGS

The method and apparatus of the invention will now be described with reference to the accompanying drawings, in which.

DETAILED DESCRIPTION

Figure 1:
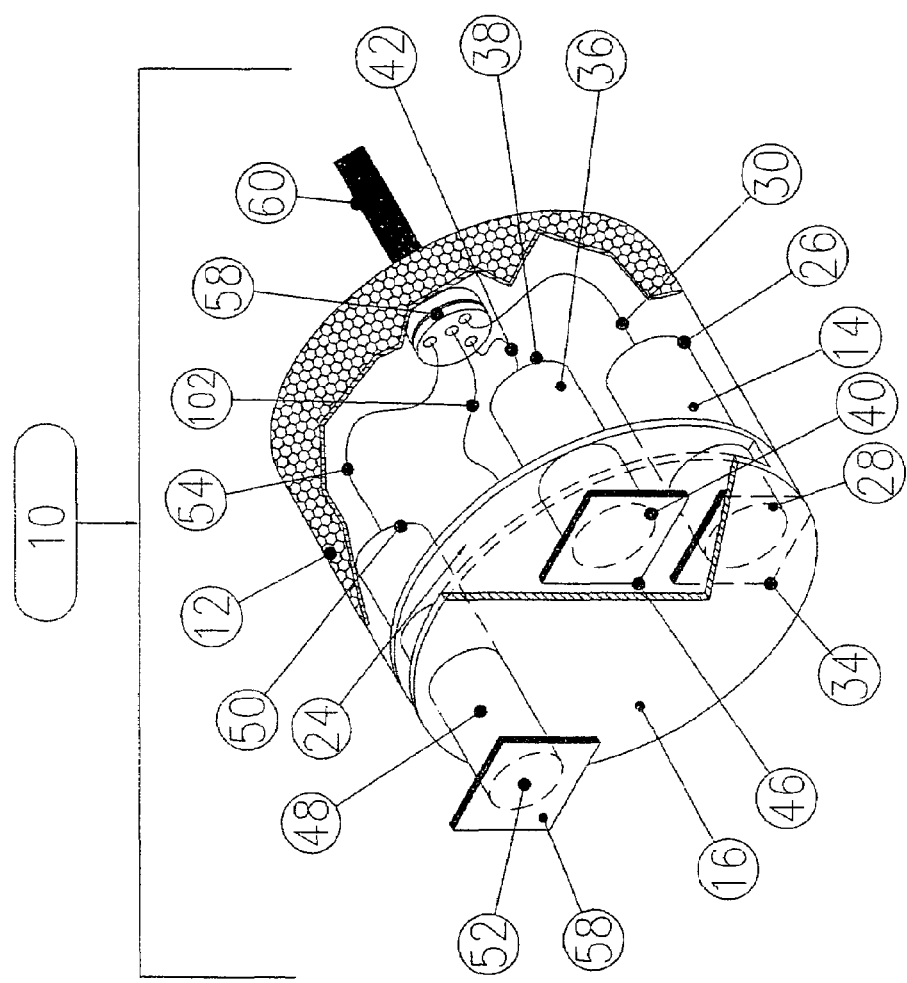
FIG. 1 is a front perspective view, partly cut-away, of an embodiment of the apparatus of the present invention.
Figure 2:
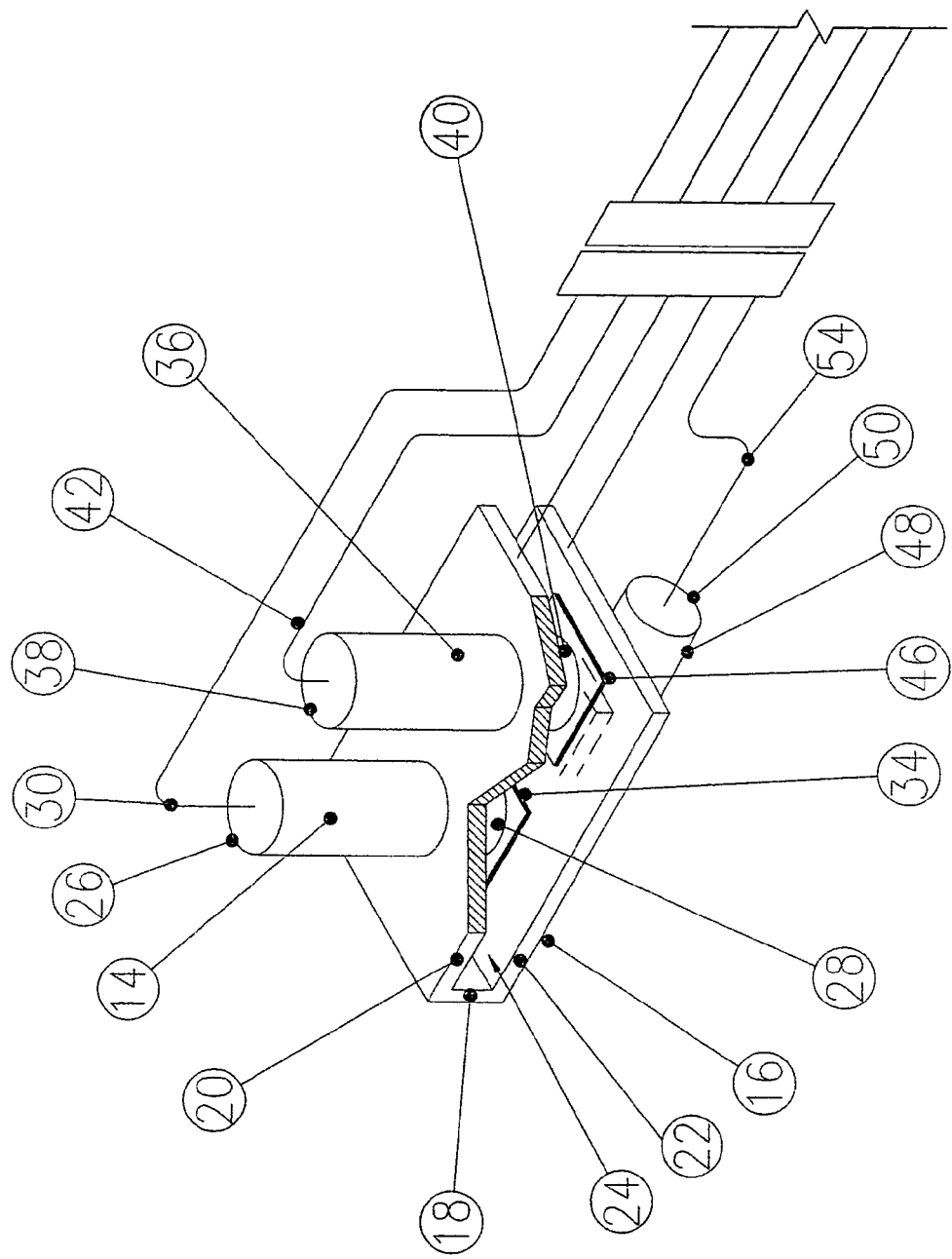
FIG. 2 is a schematic illustration of an embodiment of the application of the present invention, showing the lead wires emanating from the reference electrodes and the metal coupon.

Referring to FIGS. 1 and 2, the present invention provides an apparatus 10 for measuring the efficacy of cathodic protection process at a surface of a metal structure 64 disposed in a location where visual inspection of the metal structure 64 is rendered difficult. The apparatus is useful for measuring and controlling the efficacy of cathodic protection at an internal surface of metal containments or, for example, at an underground or submerged metal structure 64, where such metal surfaces are exposed to an electrolytic environment.

The apparatus 10 includes a metal coupon 16 which is protected in a similar manner to the metal structure 64 in order to simulate the cathodic protection of the metal structure 64. A pH/temperature reference electrode 14, and potential sensing reference electrodes 36, 48 are provided to sense an indication of cathodic protection of the metal coupon 16, and, therefore, indirectly, within the protective film at the surface of the metal structure 64.

The coupon 16 is electrically connected to the metal structure 64 by insulated conductor 102 so as to enjoy relatively the same degree of cathodic protection as the metal structure 64. In this respect, the degree of cathodic protection imparted to the metal structure 64 is simulated by the coupon 16. The coupon 16 is a single metal strip which is folded over onto itself to form a reverse band defined by a web 18 joining opposing first and second flanges, 20, 22. A simulated crevice 24 is defined by the space between the first and second flanges 20, 22. The space between the first and second flanges is up to about 1 mm between the high points of the opposing flanges. The simulated crevice may be in different forms depending on the application, and is not necessarily required to adopt the configuration illustrated in FIGS. 1 or 2.

The crevice 24 is configured to approximate the geometry of a crevice such as within the interstices in the metal structure 64. In this respect, electrochemical conditions within the crevice 24 simulate those present in the crevice of the metal structure 64, when the coupon 16 is disposed in an electrolytic environment common to that which the structure 64 is being exposed to. Crevices initially begin as corrosion pits. Depending on the metal, environment, experimental and kinetic (electrical, mechanical, etc.) conditions, corrosion pits may assume different shapes. Their mouths can be either open (uncovered) or covered with a semi-permeable membrane of corrosion products. They may be either hemispherical or cup-shaped. In some cases, they are flat welled, revealing the crystal structure of the metal, or they may have a completely irregular shape. Pitting functionality is highly complex, involving various exposure condition parameters difference in composition of the electrolyte metallurgy polarization inside the pits, and outside on the metal surface: polarization, composition and alkalinity, potential of the surrounding film, and temperature of the interface. In the extreme, the corrosion pits develop into crevices.

The pH/temperature reference electrode 14 provides a measurement of pH and temperature in the electrolytic environment proximate to the coupon 16. An insulated conductor 30 extends from the pH/temperature reference electrode 14, for electrical connection to suitable pH recording equipment 32. The pH/temperature reference electrode 14 is ionically connected to the electrolytic environment through a membrane 34 which functions to mitigate or prevent fouling of the electrode 14. In one embodiment, the pH/temperature reference electrode 14 is disposed within the crevice 24 of the metal coupon 16 to sense pH and temperature in this presumably least protected area.

In one embodiment, a first potential sensing reference electrode 36 is provided to give an indication of electric potential in the area of concern in the crevice 24. A conductor 42 extends from the first potential sensing reference electrode 36, for electrical connection to suitable potential recording equipment 44. Preferably, the first potential sensing reference electrode 36 is disposed within the most active area in the crevice 24 of the metal coupon 16 to sense electric potential. The first potential sensing electrode 36 is in ionic contact with the electrolytic environment through a membrane 46.

As a further modification, a second potential sensing reference electrode 48 is provided to give an indication of electric potential of the metal coupon 16, but outside the crevice 24. In this respect, unlike the first potential sensing reference electrode 36, the second potential sensing reference electrode 48 is disposed outside of the crevice 24 of the metal coupon 16, but proximate to the metal coupon 16. The second potential sensing electrode 48 is in ionic contact with the surrounding electrolytic environment through a membrane 46. A conductor 54 extends the second potential sensing reference electrode 48, for electrical connection to suitable potential recording equipment 56.

Each of the electrodes 14, 36, 46 are positioned as close to coupon 16 surface as possible. Whereas most of the voltage drop in the ionic circuit between the anode and cathode occurs within the protective film on the cathode surface, the closer the reference electrodes, 14, 36, 48 can be to the cathode surface (the coupon 16 surface) the more representative will be the measurements of potential and alkalinity and temperature of a polarized surface.

Each of the first 36 and second 48 potential sensing reference electrodes may include one of many typical sensing electrodes known in the art, such as the following: silver/silver chloride reference electrodes, calomel reference electrodes, copper/copper sulphate reference electrodes, redox potential reference electrodes, and very high purity zinc reference electrodes.

To facilitate movement of the apparatus 10 to the desired location for measurement and control of the efficacy of cathodic protection being applied at the metal surface of structure 64, and the metal coupon 16 including reference electrodes 14, 36, 48 integrated in a singular housing 12. The metal coupon 16 is coupled to and disposed externally of the housing 12. The reference electrodes 14, 36, 48 are disposed within the housing 12 and extend externally of the housing 12 by penetrating the external surface of the housing 12. The conductors 30, 42, 54 combine within the housing 12 into a wiring harness 60 via a suitable conductor harness connector 61 disposed within the housing. The conductor harness 60 penetrates the external surface of the housing 12 for connection to the recording equipment 32, 44, 56.

Figure 3:
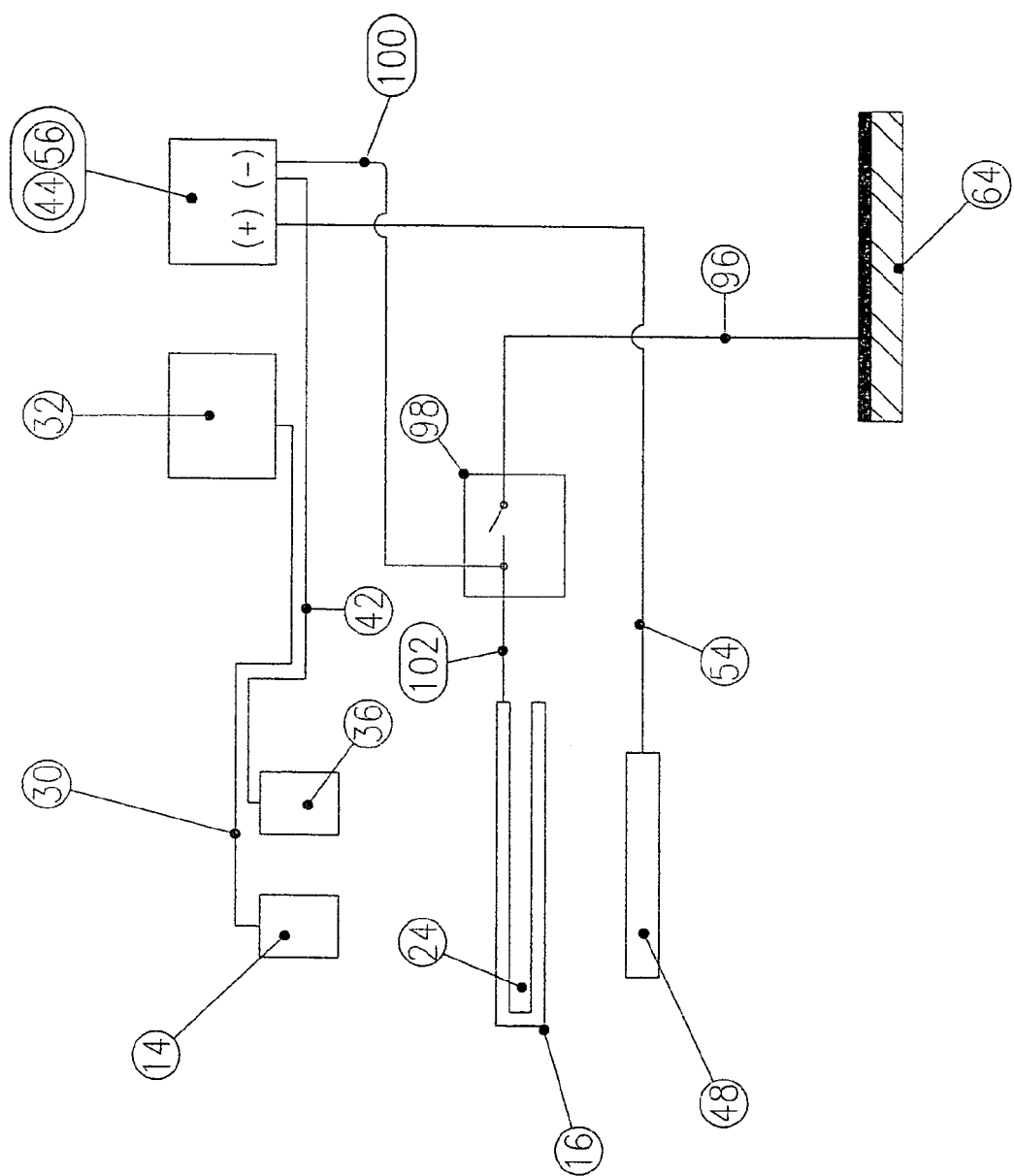
FIG. 3 is an electrical schematic illustration of an embodiment of a system of the present invention, wherein the apparatus illustrated in FIG. 1 is used for measuring the efficacy of a cathodic protection process at a surface of a metal structure.
Figure 5:
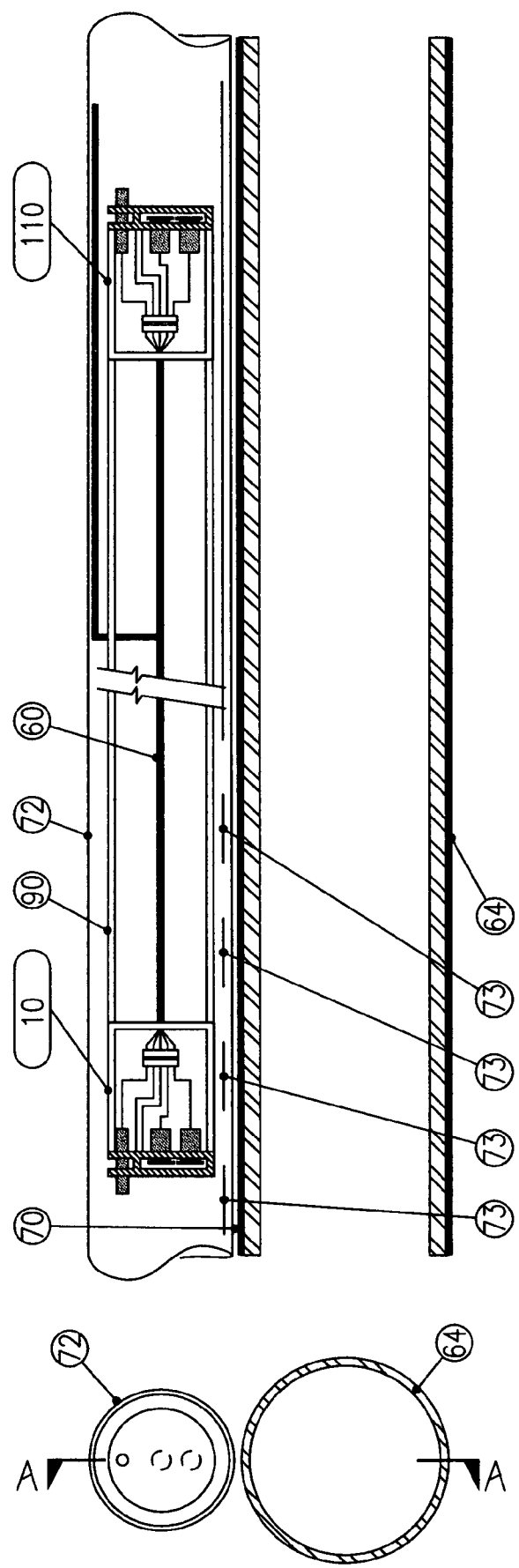
FIG. 5 is an enlarged view of a section of the embodiment of the system illustrated in FIG. 4, showing two metal coupons disposed for travel in a conduit for measuring the effectiveness of cathodic protection of a metal structure proximate to the conduit.

Referring to FIGS. 3 and 5, the apparatus 10 is used in a system 62 to measure the efficacy of corrosion protection at a surface of a metal structure 64, the structure 64 by being disposed in an environment rendering visual inspection difficult. An example of such a metal structure 64 is an underground pipeline. Cathodic protection of a corroding surface of the metal structure 64 can be accomplished by coupling the negative terminal of a voltage and current source to the metal structure 64. An auxiliary anode is electrically coupled to the positive voltage terminal of the voltage and current source to impress DC electrical current from the axillary anode to the targeted surface of the metal structure 64 and returning it to its source. The current is impressed until the entire surface of the metal structure 64 polarizes to delete all anodic areas, thereby preventing electrical current from transferring between different surface areas of the metal structure 64. Ideally, effective cathodic protection means the metal structure should not corrode so long as the external current is maintained because species environment toward the cathode (i.e. the metal structure surface being protected), whereas species which promote corrosion, and have a tendency to be oxidized travel toward the anode.

It is to be understood that other means for applying cathodic protection are available, including means for producing galvanic current by coupling a sacrificial anode to the metal structure 64 to be protected in the subject electrolytic environment (a sacrificial anode could be any metal that is less noble than the metal to be protected, i.e. magnesium is a sacrificial anode for steel whereas steel is a sacrificial anode for copper also the same metal immersed in different environments can be sacrificial to itself i.e. steel in soil is anodic to steel in concrete.

To measure the efficacy of cathodic protection process at a metal structure 64, one embodiment of the present invention provides a system 62 comprising a cathodically protected metal structure 64, an anode or anodes 66, any one of the above-described embodiments of the apparatus 10, and one or both of pH recording equipment 32 and potential recording equipment 44 and 56. As a further modification, a voltage and current source (cathodic protection rectifier) 68 may be additionally provided to effect DC current. The metal structure 64 is electrically coupled to the negative terminal of the potential recording equipment 44, 56 and to the negative terminal of the voltage and current source 68. The anode 66 is electrically coupled to the positive voltage terminal of the voltage and current source 68 to impress direct electrical current from the auxiliary anode 66 to the targeted surface 70 of the metal structure 64 before returning it to its source. To measure pH and electric potential in the environment under the cathodic protection condition, the apparatus 10 is disposed in an electrolytic environment common with that in which the metal structure 64 is disposed and from which the metal structure 64 is being cathodically protected. In this environment, the apparatus 10 is disposed as close to the metal structure 64 as possible so that the conditions which the apparatus 10 is exposed approximate those to which the metal structure 64 is exposed. The metal coupon 16 of the apparatus 10 is electrically connected to the metal structure 64. The reference electrodes 14, 36, 48 of the apparatus are electrically connected to their associated recording equipment 32, 44, 56 in the manner above-described. The recording equipment 32, 44, 56 may be located either in the electrolytic environment or remote from the electrolytic environment, depending on the choice of recording equipment.

The pH reference electrode 14 measures the alkalinity of the film formed proximate the metal coupon 16 and, in one embodiment, in the crevice 24 of the metal coupon 16. Such alkaline film forms on the surface of these areas upon impressing direct electrical current on the metal coupon 16. The pH value of the alkalinity of the film reflects the level of cathodic protection effectiveness at the surface of the metal coupon 16. In turn, this is an indicator of the level of cathodic protection of the metal structure 64, as the metal structure 64 is electrically connected to the metal coupon 16 and, therefore, enjoys substantially the same degree of cathodic protection.

Each of the first and second potential sensing reference electrodes 36, 48 measure electric potential in each of their respective areas of contact to the surrounding electrolyte. The first potential sensing reference electrode 36 measures electric potential within the metal coupon crevice 24. The second potential sensing reference electrode 48 measures electric potential proximate the metal coupon 16 but outside of the crevice 24. Each of these electric potential measurements provide a secondary indication of the effectiveness of cathodic protection applied at both the metal coupon 16 and the metal structure 64.

Figure 4:
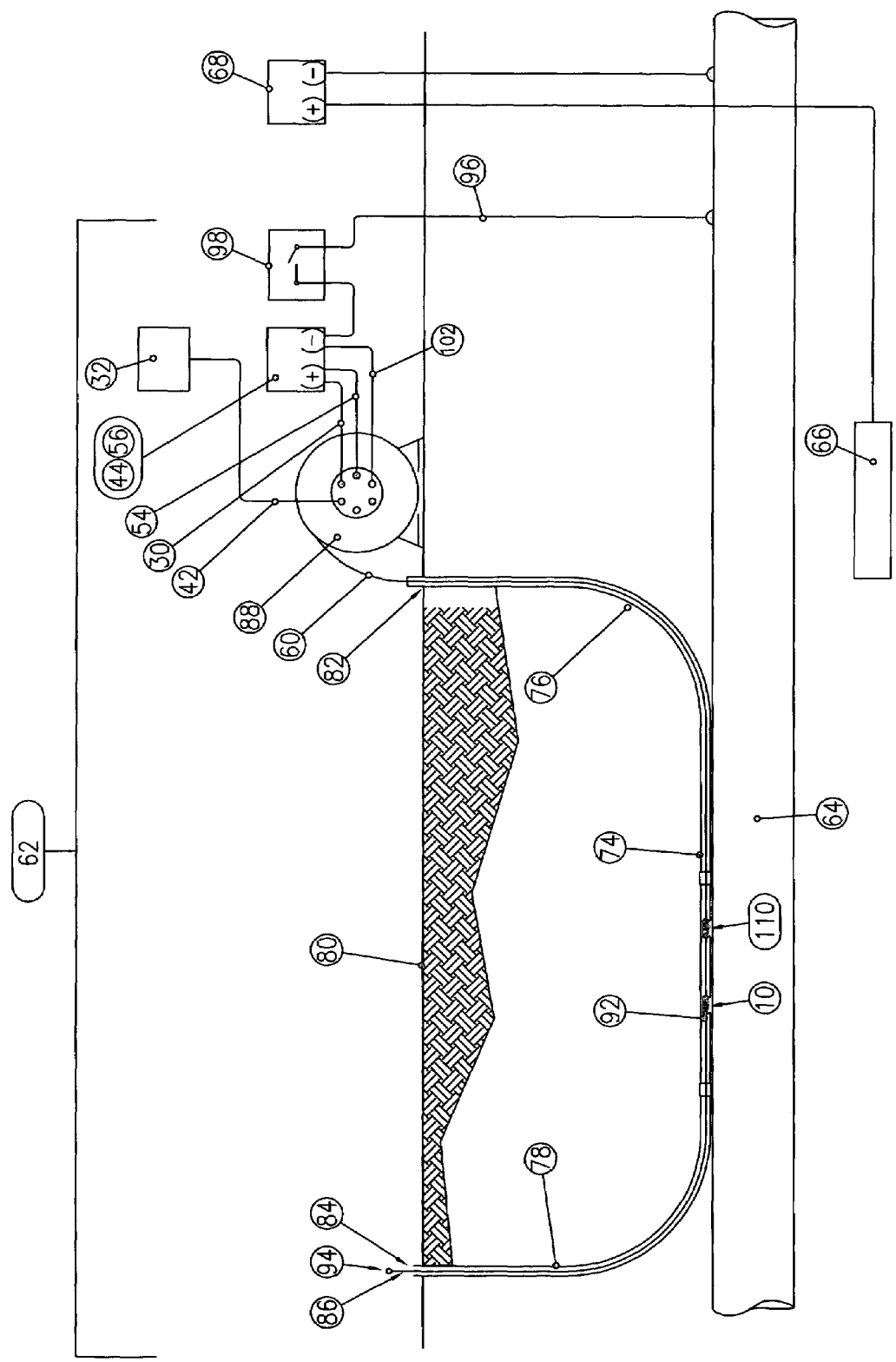
FIG. 4 is a schematic illustration of an embodiment of a system of the present invention.

Referring to FIGS. 4 and 5, in another embodiment, a system 62 is provided having an elongated, perforated, non-metallic conduit 72 which extends across and proximate to various regions on the surface 70 of the metal structure 64.

The conduit 72 can be comprised of materials such as polyvinyl chloride. The perforations 73 can be replaced by a membrane or a porous plastic strip moulded into the conduit 72.

The conduit 72 is intended to provide a means for the apparatus 10 to travel from an accessible location to a remote location such as a soil electrolyte where pH and electric potential measurements are required, and specifically proximate to various regions on the surface 70 of a metal structure 64 disposed in a soil electrolyte. The closer the apparatus 10 is to the structure 64, the more representative are the measurements. Locating the apparatus 10 in close proximity to the structure 64 allows the apparatus 10 to more closely approximate the conditions of the structure 64 wherever the apparatus 10 may be positioned. The proximity of the apparatus 10 to the metal structure 64, is limited by the physical geometry of the conduit 72, such as the will thickness. The conduit 72 can be disposed directly above, or beside, or below, or at any point along the surface of the structure 64, and includes a conduit 72 alongside the surface of the structure 64 (such as spirally wrapped around a pipeline of supporting legs on an offshore platform).

To realize this deliberate orientation relative to the surface 70 of the metal structure 64, and with reference to an embodiment where the metal structure being protected is disposed in a sub-surface soil environment, a section 74 of the conduit 72 is provided underground proximate to the metal structure 64. This underground section 72 joins a first 76 and a second section 78, each of which extends from the ground surface 80 and are open to the surface 80 at respective first and second ends 82, 84. The apparatus 10 is pulled through from the first end 82 to the second end 84 by a rope or cable 86 or other similar device from the second end 84. A reel 88 with slip ring hub is provided proximate to the first end to carry the multiconductor and wiring harness 60 and provide a means for controlling the amount of slack required in the wiring harness 60 to facilitate travel of the apparatus 10 through the conduit 72.

The conduit 72 is perforated to facilitate entry of electrolyte of the underground soil and, thereby, effect ionic contact between this electrolyte and the metal coupon 16, as well as the reference electrodes 14, 36, 48. The conduit 72 is configured to minimize voltage drop error in the potential measurements. In this respect, the conduit 72 substantially dielectrically shields the apparatus 10. The conduit 72 comprises non-conductive material, such as PVC or other plastics (eg. polyethylene).

The electrical connection between the metal coupon 16 and the metal structure 64 includes a timed circuit breaking switch disposed therebetween. The switch permits intermittent interruption of current, and thereby facilitates the measurement of both the polarized potential and the rate of depolarization proximate the metal coupon surface, which is another indicator used to assess the efficacy of the cathodic protection process.

In another embodiment, more than one apparatus 10 can be disposed within the conduit 72 and electrically connected to the necessary recording equipment 32, 44, 56 and to the metal structure 64. This enables simultaneous measurement of pH, temperature, and/or electric potential at different locations and proximate to different regions of the surface 70 of the metal structure 64. Referring to FIG. 5, two apparati 10, 110 are provided. The two apparati 10 are connected by a connector 90. The connector 90 is a non-conductive semi-stiff cable or rope or housing extending at either end from each of the apparati 10, 110 for the purpose of maintaining a set distance between the apparati. The connector 90 can also be configured to carry a multi conductor harness 60.

In operation, one or more apparati 10 are connected to one end 92 of a rope 86 and the rope 86 extends through the conduit 72 and has its second end 94 emerging at the access location 80 from the second end 84 of the conduit 72. The apparatus 10 is further connected to the multi conductor harness 60. The pH and voltage data lead wires 30, 42, 54 are connected to the slip ring terminals on the reel 88. An insulated conductor cable 96 from the structure 64 under surveillance is connected to a terminal of a circuit interrupter 98. A separate insulated conductor cable 102 from the remaining terminal of the circuit interrupter 96 is connected to the coupon terminal on the reel 88. A further insulated conductor cable 100 from the structure under surveillance is connected to the potential recording equipment (see FIG. 3).

To commence pH and voltage measurement, the pH and potential recording equipment 32, 44, 56 and the circuit interrupter 98 are actuated. The apparatus 10 is inserted into the first end 82 of a conduit 72 and is pulled therethrough by continuous tensioning of the rope 86 from the second end 84 of the conduit 72. In one embodiment, the apparatus 10 is advanced at a steady rate.

While the apparatus 10 is advanced through the conduit 72, date is collected by the recording equipment 32, 44, 56. Two types of data are collected: current-applied potentials and polarized (current interrupted) potentials. Current-applied potentials are measured when the circuit is closed (i.e. when the circuit interrupter 98 is closed). Polarized potentials are measured when the circuit is open (i.e. when the circuit interrupter 98 is open, thereby interrupting the current). The circuit interrupter 98 can be set to alternate between open and closed conditions at a desired frequency (i.e. current on condition and off condition of a desired duration). Current-applied potentials indicate areas of the structure 64 where current density is too much or too little to produce a more or less negative potential than desired. Polarized potentials indicate the cathodic protection efficacy of the polarized film produced on the structure surface 70.

Data obtained from these close proximity measurements are much more accurate than the data representing the average data remotely obtained conventionally for buried or immerse pipeline. Wherever the apparatus 10 is maneuvered through the perforated non-metallic conduit 72 in close proximity to the metal structure 64, the obtained data greatly increases the ability to assess the alkalinity of the permeated protective film, the coating performance, and to be more fully assured of maintaining the safe targeted minimum/maximum EMF/pH value range for a safe state of equilibrium for immunity to corrosion at all points within a targeted polarized potential range.

The apparatus 10 disposed within the conduit 72 facilitates proximity measurements synchronously of the surface pH value and the polarized potential surface both within the protective film retained on the coupon surface at the structure, and/or detect any lack of sufficient cathodic polarization, and do so without significant 'IR' drop error such as occurs, for instance, wherever foreign DC current interferences are significant. This would allow confirmation and verification (instead of estimation by extrapolation of this data to asses film quality) with respect to the actual film on the surface of the metal structure. Note that the apparatus 10 may be disposed adjacent to a predetermined area of foreign current entry or discharge and in connection with controlling a DC current source positioned within the same area may polarize this specific area, thus reducing, preventing or obviating the tendency for foreign sourced stray DC current to enter or discharge to earth at this area.

The apparatus 10 would also facilitate measuring variations of the current-applied potential near the adjacent primary structure, and to synchronously compare with relatively minor variations of the current-interrupted or polarized potential of the coupon surface without necessarily interrupting all source(s) of protective current providing cathodic protection at the surface of the metal structure 64.

The apparatus 10 may be equipped with various other types of reference electrodes, either positioned external to the metal coupon to sense the direction of current flow (i.e., correctly towards or conversely away from the surface of the primary structure), and/or by spacing sets of coupons with paired electrodes apart to detect areas provided with less effective protective film or cathodic protection.

Measurement of the current returned from the coupon 16 to the metal structure 64 can be used to assess the conductance of the coating on the metal structure 64 and/or the protective film at accessible locations relative to a second coupon and the availability of ample protective current density at all points throughout the length of the perforated conduit 72.

Capacitance measured in coulombs of the in-situ polarized film developed over the coupon surface may also be measured during cathodic depolarization rate or polarization rate testing, and/or by utilizing capacitors to store, and/or at intervals discharge the stored energy of the polarized surface capacitance.

This information may also be used in the following ways wherever electrodes are fixed within a perforated non-metallic conduit placed near an immersed structure, such as an underground or offshore pipeline with cathodic protection applied.

Throughout the sensor conduit data from the apparatus 10 can be used to monitor as accurately (as in nearly 'IR' drop error-free test points) the polarized potential and the pH value within the polarized film produced on the coupon surface or in the simulated crevice allowing, assessment of the film quality on the adjacent structure.

The apparatus 10 facilitate measuring the current-applied potential at the adjacent structure as well as the current-interrupted potential at the coupon 16 without necessarily interrupting all maintenance current sources providing cathodic protection at the metal structure surface.

The apparatus 10 does not necessarily require a rope 86 for mobility, such as where the apparatus can be self-propelled by an on-board drive mechanism. Also, a multi-conductor harness is also not necessary where data could be communicated wirelessly. In such cases, a single metallic contact must be maintained between the structure 64 and the coupon 16 in such cases. In other cases, the conduit 72 may not be required, such as where the electrolytic environment form which the structure 64 is being protected, although rendering visual inspection difficult, still makes it possible for mobility of the apparatus 10. An example of this case is where the electrolytic environment is an aqueous fluid within a container such as a tank or other fluid containment structure (such as piping), and the structure 64 is the fluid containment structure.

Figure 6:
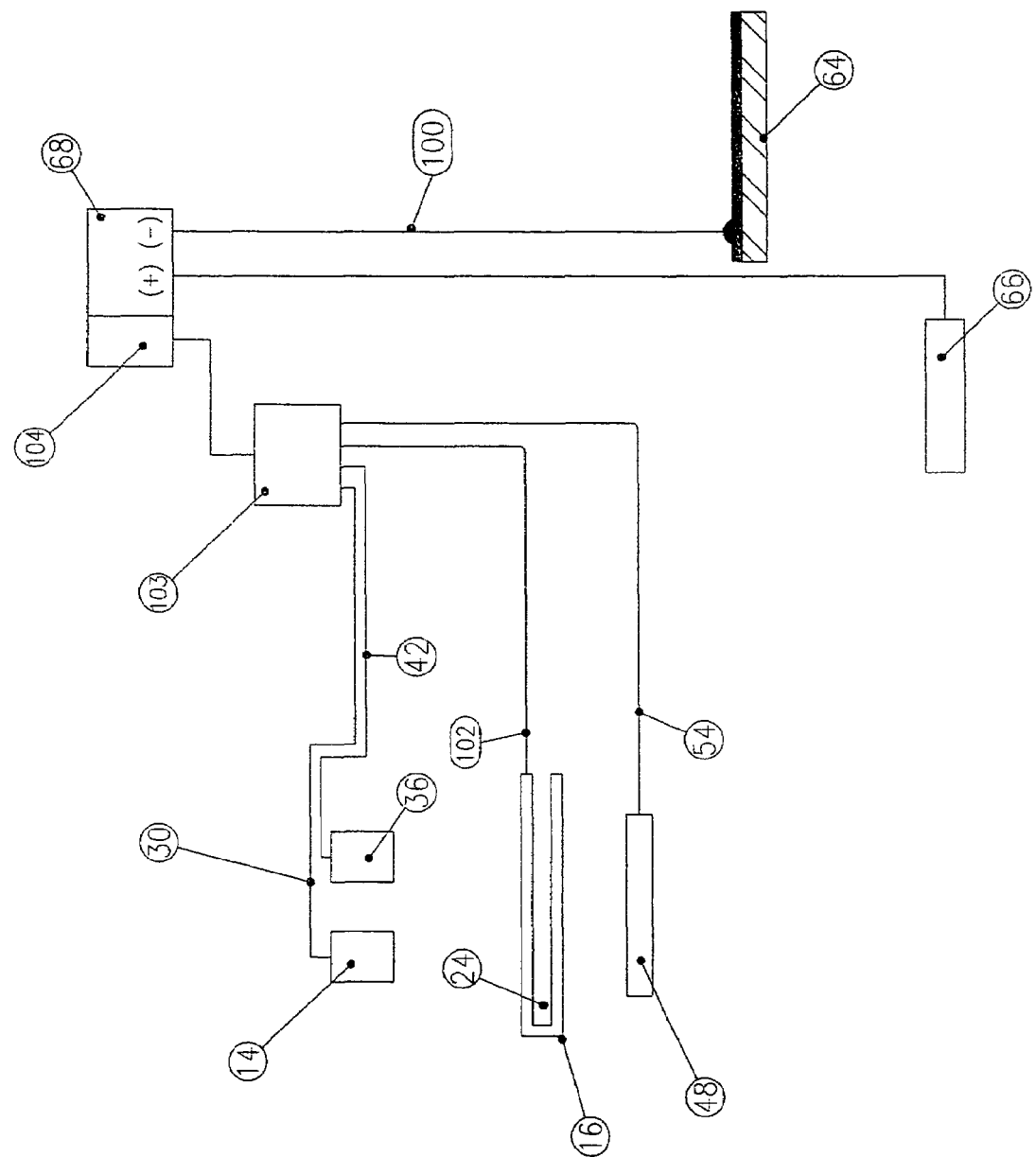
FIG. 6 is an electrical schematic illustration of a further embodiment of the system of the present invention, wherein the apparatus illustrated in FIG. 1 is configured to control the output of a protective current source.

FIG. 6 illustrates a further embodiment of a system 162 of the present invention, whereby the current output from an external source such as a cathodic protection rectifier 68 may be increased or decreased via a control module programmable logic controller. Data sourced from the apparatus 10 may also be used. to control the alkalinity at the surface of the metal coupon 16 and the surface of the structure 64 by adjusting the impressed current density applied at the surface of the structure 64. The built-in reference electrodes 36, 48 and the surface sensing pH electrode 14 may be used to precisely control a current output to provide a current density to meet both of the targeted criteria indicated in potential/pH diagrams, such as for an ion and austenic stainless steels and other metal surfaces. Quality assurance measurements at the protected surface of the metal coupon 16 should correspond in a close relationship with those obtained at the surface of the protected primary structure 64. The impressed current applied can be increased or decreased (via a programmable logic controller device 103 connecting the structure potential sensing reference electrodes 36, 48 to the control module 104 for the cathodic protection rectifiers) in accordance with the targeted safe minimum/maximum alkalinity measured by the pH reference electrode 14. For example, if the intent is to prevent corrosion of iron, the primary control range may be 11.5±0.5 pH whereas the corresponding polarized potential range may be −1050 mV to −1100 mV (CSE). (Note: presently auto-potential controlled rectifiers do not sufficiently compensate for the varying temperature of the metal structure interface and are usually controlled by sensing the potential measured by a single reference electrode installed at a fixed location.

Figure 7:
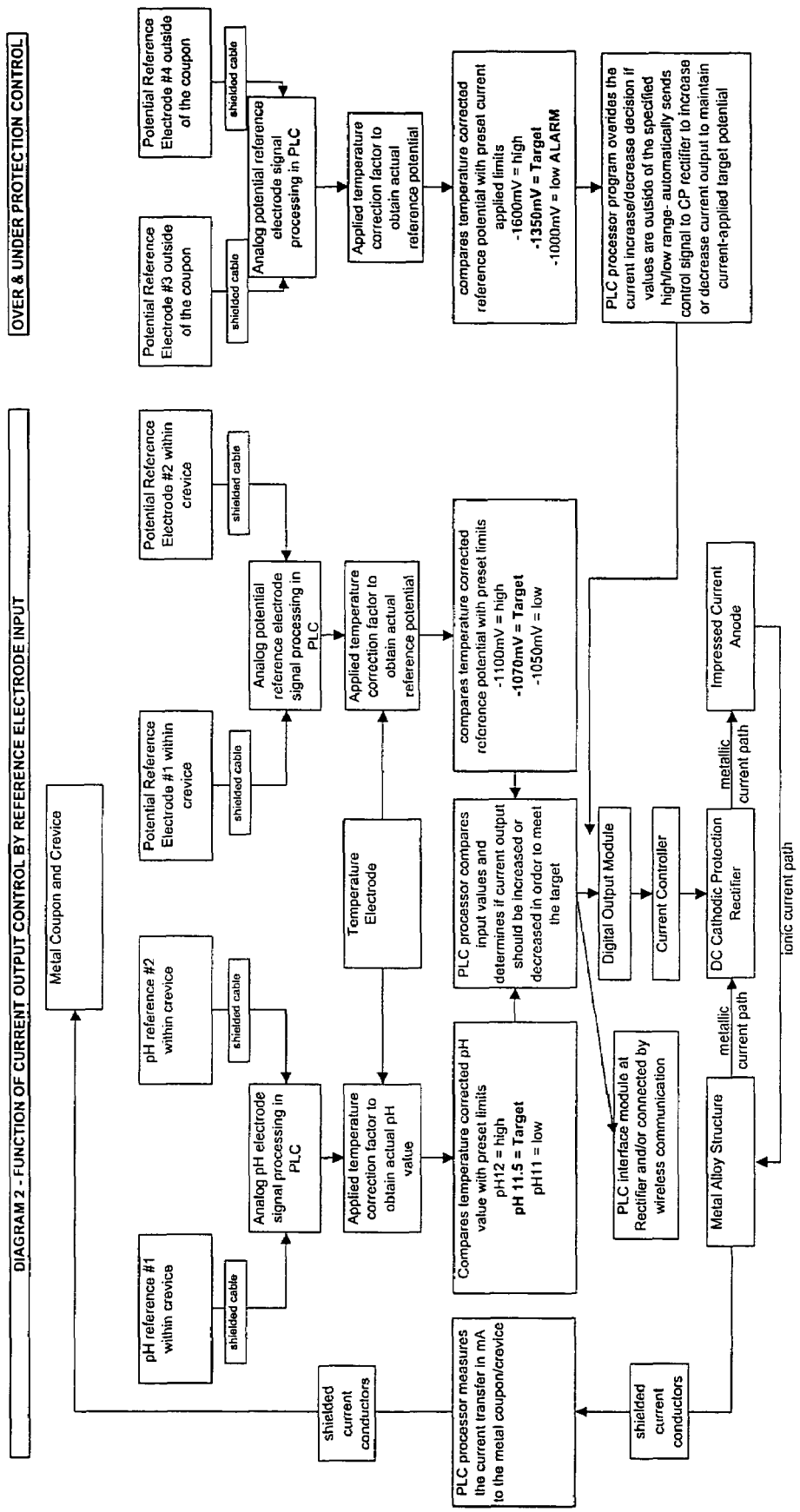
FIG. 7 is a flow chart illustrating a method of controlling cathodic protection in accordance with an embodiment of the present invention.
Figure 8:
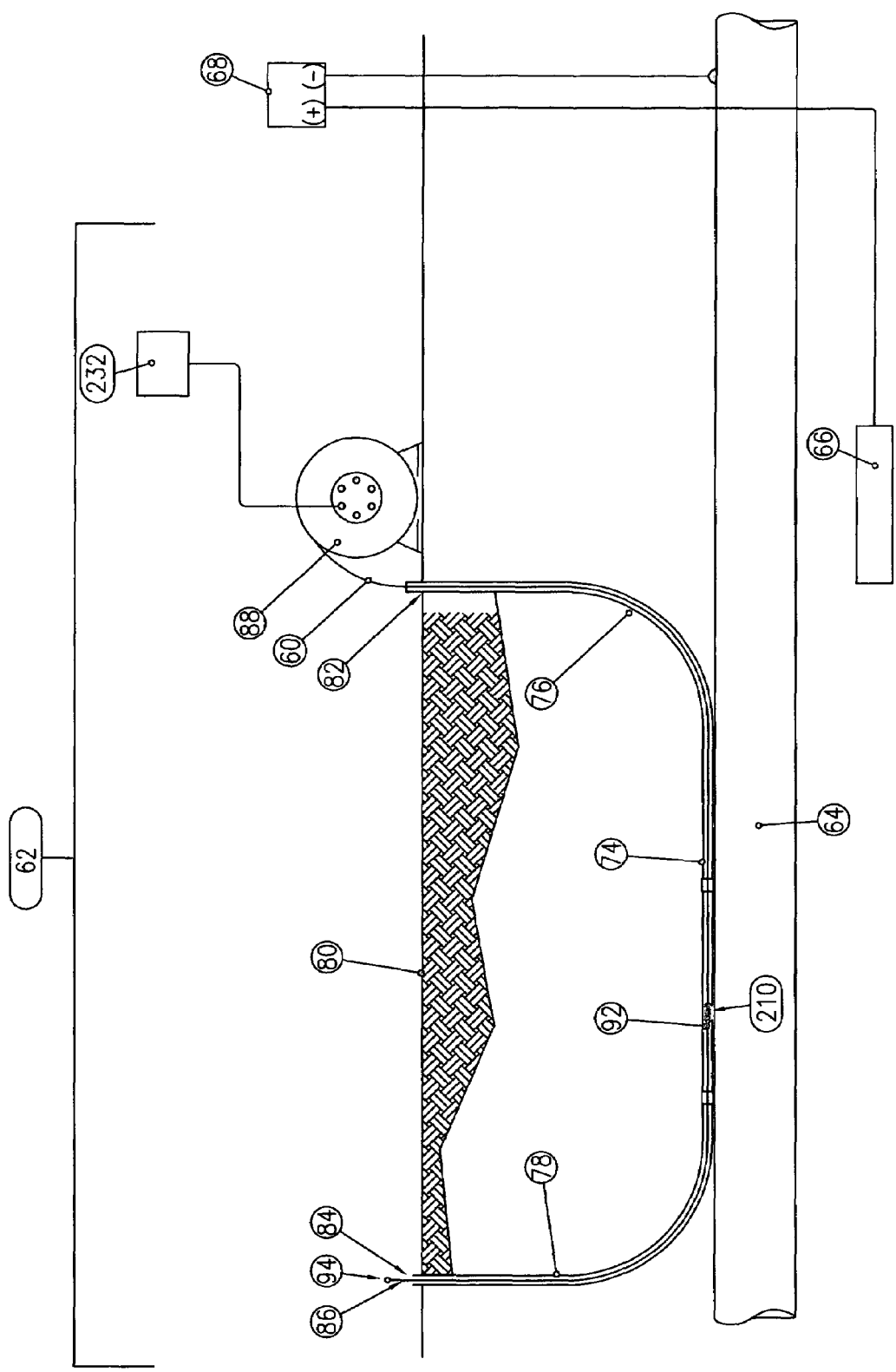
FIG. 8 is a schematic illustration of another embodiment of a system of the present invention.

FIGS. 7 and 8 are flow charts illustrating methods of controlling cathodic protection being applied to the metal structure 64 and using a system of the present invention, such as that illustrated in FIG. 8.

It should be noted that a propriety program allowing the user to select pH/potential high, low limits and target values must be programmed prior to the following operations.

The programmable logic control (PLC) device (or other suitable programmable input, output device) uses analog input signals from all references (pH, potential, temperature) disposed within the crevice and at the coupon 16, to control the current output of a suitable DC current source. These signals are first processed and corrected for temperature variations at the coupon 16 by applying a correction factor based on a predetermined formula or provided for by the reference electrode manufacturer and included in the PLC program.

The PLC program then compares the temperature corrected pH/potential data from within the crevice with the user selected pH/potential limits/targets and sends an output signal (analog or digital depending on the current controller) to a current controller for the DC current source to either maintain, increase or decrease the present current output based on a preprogrammed algorithm. Prior to sending a signal a comparison is made by the PLC of the present temperature corrected signals indicating the current-applied potential exterior to the coupon with the limits pre-selected by the user. Should this potential be outside of the limits, the PLC will instead signal the current controller to either increase or decrease the current output based on a separate algorithm until the current-applied potential is within the pre-selected limits.

In another embodiment, instead of controlling the current-applied potential to indirectly control the efficacy of cathodic protection, in cases where cathodic protection is effected ("effected" is understood as inducing a partial contribution to the overall cathodic protection of the metal structure 64) by chemical treatment, such as by the method disclosed in U.S. Pat. No. 5,174,871 which is herein incorporated by reference, the PLC 103 can respond to data sourced from the coupon 16 by adjusting the degree of chemical treatment. Some buried metal structures cannot be properly cathodically protected from corrosion, for example, where the surfaces of such buried structures are buried in sand and similar granular backfills, their aerated topside surfaces often require about 25 times the protective current density of their anaerobic bottoms. As a result of oxygen diffusion where protective coatings have failed or do not exist, it is often proven difficult or not feasible to prevent corrosion of bare and poorly coated tanks by applying cathodic protection with either galvanic and/or impressed current uniformly over entire metallic surfaces. It has been found that the chemical de-aeration of the backfill in which the metal structures are buried, by adding to the backfill, an electrically conductive composition containing calcium, magnesium and/or silicate compounds for producing an alkaline pH to precipitate in-situ carbonate coatings or "concretions" of the metallic surface, with concurrent depletion of oxygen, facilitates uniform cathodic protection for underground steel structures. In this respect, the chemical de-aeration of the backfill comprises adding, to the backfill, calcium hydroxide in an amount effective to increase the pH of the backfill to above 8.0, and applying a protective current to create a polarized electrical potential between the surface of the metal structure and its backfill, whereby the metal structure is maintaining negative relative to the backfill. Preferably, the composition comprises by weight, from about 75–90% calcium hydroxide, from about 3–20% calcium silicate, and an effective amount of calcium nitrite to remove oxygen in the mixed solution. Up to 50% by weight of the calcium hydroxide can be replaced by magnesium hydroxides or calcium silicate. The calcium nitrite is present in an effective amount of from 2% to a maximum 5% by weight for removal of oxygen.

The control mechanism of this embodiment of the present invention relates to the controlled addition of the de-aeration base solution, in response to data collected by reference electrodes 14, 36, and 48. A conduit is inserted within the sensor conduit to effect the transfer of the de-aeration base solution from a storage tank to the area of concern via the tube. The mixture then percolates through the perforations in the sensor conduit to infiltrate the surrounding electrolyte or, in the case of a buried pipeline, the backfill. The mixture then de-aerates and increases the electrolyte (backfill) pH to help shift the metal surface towards the corrosion immunity EMF/pH region. The mixture could be continuously added at a rate that would control the surrounding electrolyte pH whenever a DC stray current continues to discharge and deplete the alkalinity.

The apparatus 10 could also be used as proposed in conjunction with proprietary software and modem connections to remotely measure and assess the rate of cathodic depolarization and other parameters to evaluate performance characteristics. It is understood that use of the apparatus 10 of the present invention is not limited to measurement of the efficacy of cathodic protection imparted to a metal structure in a sub-surface soil environment. The apparatus 10 can be used to measure the efficacy of cathodic protection imparted to a metal structure in other environments where visual inspection of the metal structure is difficult, such as metal structures submerged in a liquid environment, for example, marine and offshore structures in an aqueous sea water environment and/or in process equipment in various aqueous electrolytes.

This invention has various other safe and cost-effective applications. The economic integrity maintenance life span of underground and offshore pipelines has often been limited by aging effects to an average of about twenty to twenty-five years. Aging has been primarily attributable to soil stresses and erosion corrosion and overprotection and underprotection at the bare steel or coated steel interface. Maintenance costs generally increased as distribute galvanically sacrificially anodes (about 1 m distant) failed to maintain effective cathodic protection due to decreasing output of protective current upon approaching consumption, and/or the increasing impressed current density from external remote anode sources within a similar time frame. Adverse effects include overprotection and underprotection and/or resulted in impressed DC stray current interferences at foreign pipelines and other metallic structures sharing the soil or water environment. Likewise, foreign DC impressed current interferences at pipelines and metallic structures must be mitigated, particularly those sourced from dynamic movements in foreign DC traction systems.

Heretofore, deterrents to locating impressed current anodes in proximity to the structure interface included the dangers of coating disbondment and/or hydrogen embrittlement by over-protection and by the production of corrosive gases (i.e., carbon dioxide and sulphur dioxide in soils and chlorine, in seawater) and acids, which tended to increase the loss of protective coating and, thus, increase maintenance costs and decrease the efficacy of cathodic protection. Instead, through utilization of this conduit to impress protective current without adverse effects proximate to the interface, the pipeline life expectancy may be doubled or extended indefinitely.

In one embodiment, to mitigate or to obviate or prevent aging effects, the impressed current sourced from an anode immersed within potassium and sodium hydroxide in isolated plastic containment can be equipped with a cation exchange membrane and/or a porous membrane, or an internal pipe membrane containing a number of anodes or a continuous anode can be inserted proximate to the interface within the sensor conduit.

The present invention can be used to obviate or prevent the adverse effects from DC stray currents. The mitigation of stray current corrosion on buried metal structures is a major problem where rounded DC systems are operating. Pipelines represent an enormous conductor of low electrical resistance with large areas in contact with the earth that collect and discharge relatively high DC stray current. The lack of such preventative measures in some stray current areas has resulted in serious leaks in new pipelines in a matter of months after their installation. Some of the problems associated with D.C. stray currents are described in R. M. Keller, Stray Current Mitigation Bonds and Reverse Current Switches, Proceeding of the Sixteenth Annual Underground Short Course, West Virginia University:

"Grounded DC power systems are found in trolley lines, mining cars and equipment, cathodic protection systems, etc. In a grounded DC system, the load is also grounded. The current returning from the lead to the negative terminal of the generator now has tow available paths. One path is through the negative return cable and the other path is through the ground. The pipeline offers another parallel path for the current returning to the generator. The section of the pipeline that is picking up current will tend to be cathodically protected, while the section losing the current through the earth to the generator will corrode. On well-coated pipelines, the major portion of this current is lost at holidays in the coating, thus concentrating the current loss and the metal loss area which could cause more rapid penetration of the pipeline."

Practical consequences are described in M. T. Hogan, Basic Electrical and Corrosion Fundamentals included in Pipeline Corrosion, 43$^{rd}$ Appalachian Corrosion Short Course, West Virginia University, 1998:

"If, for example, 5 milliamperes flowed off a coated steel pipe at a break in the coating that was one-inch in diameter, $\frac{1}{10}^{th}$ of a pound of metal would be removed and penetration would occur." Note "that a one-inch diameter hole in the surface of normal 30-inch pipe weigh approximately 0.8 pounds."

The presence of low negative or any positive pipe-to-soil voltages in an indication that a foreign structure may be nearby and drawing from the surveyed structure. This is recognized in R. L. Seifert, Practical Interference Current Testing on Underground Metallic Structures, 16$^{th}$ Annual Appalachian Underground Corrosion Short Course, West Virginia University:

"Many companies feel that any positive pipe-to-soil voltage swing of less than 10 millivolts is tolerable", and "in the majority of cases where voltage swings are less than 10 millivolts . . . negligible interference exists."

When a suspected current source is found, attempts should be made to interrupt it and observe its effect on the interfered structure to ascertain that the suspected source is the cause of the abnormal pipe-to-soil voltage readings. The site where maximum positive change of voltage occurs when source current is applied is the geographical location of the maximum exposure.

The electrical drainage of underground structure systems is complicated because of reversing conditions. It would be necessary to place reverse current switches in all such connections, in order to prevent current delivery to the affected structures at times of reversals (see D. W. Barron, Corrosion Control on Water Systems; Electrolytic Versus Galvanic Corrosion Action, Proceedings of the 0$^{th}$ Corrosion Short Course, West Virginia University).

It is possible to connect the subject metal structure, such as a pipeline, by a zero resistance metallic bond to a DC generator ground cable with a view to removing all the stray current from the pipeline by way of its bond so that the pipeline would, therefore, carry a larger percentage of the total generator current than before. However, there are a number of reasons for not doing this; a few of these reasons are:

1. In many instance, the generator ground is a considerable distance from the pipeline;
2. Interference with other underground structures in the area may be increased;
3. Over-drainage may not be equitable where the source of the stray current is a cathodic protection system on a foreign structure, and
4. Where the stray current load is variable and where there is a possibility of a current reversal in the bond, it is necessary to install some sort of electrical blocking valve or switch to prevent these reversals in bond current". (Reference 1) "In practice, the design of bonds is not a simple matter. Furthermore, stray currents tend to be dynamic in nature, with the direction of current reversing from time to time." In all such cases, simple bonding is insufficient, and additional installation of diodes will be required. In some countries, the outdated practices of deliberately bonding neighbouring buried metallic structures to the real return current prevail. This approach is generally unsatisfactory, because a large amount of stray current enters the ground that cannot be controlled in complex systems (R. Rosseau, Corrosion Handbook).

Increased attention is being paid to imparting better stray current control. For example, G. A. Jacobson, Materials Performance, June 2001, stray current control in the context of rail transportation systems. There, it is recognized that "the drainage technique must only be used with extreme caution". Because nearby metallic structures which are not protected may be endangered, possibly leading to serious corrosion, "control of the protection may be made by simple measurement of the electrode potential of the piping which at all points should be permanently below the protection potential. This generally about −0.62 Volts with respect to the standard hydrogen electrode", i.e., −938 mV to the standard copper sulfate/copper sulfate (saturated) reference electrode (CSF). Also, wherever stray current corrosion concentrates, usually in the vicinity or at crossings with foreign metallic structures, the steel weighing 0.000281 pounds per square inch and one (1) mil thick is consumed annually.

Thus, measurement criteria should be established to determine, predict, and correct any resulting direct current interference problems. Moreover, it has been noted at the LaQue Centre that corrosion of carbon steel increases by approximately fifty (50) percent between the winter (average temperature 7° C.) and summer (27° C. to 29° C.) months. Evidence from work on steel in portable waters suggests that the temperature effect is more important and that corrosion, for steel, will increase with temperature. Sulfate reducing bacteria (SRB) associated with Microbiologically influenced Corrosion (MIC) is completely stifled at pH 12.5. In the absence of sulfate, some strains can function as fermenters and use organic compounds. "Moreover, all micro-organisms have an optimum temperature range for growth" (R. Rosseau, Corrosion Handbook).

There are two main bodies of thermodynamic data; one is the electromotive series, the other is the collection of Pourbaix diagrams. These diagrams define the areas of pH and potential in which particular minerals may be expected to dissolve, and where passivity is indicated as s possibility. However, the case of immunity is not ambiguous—corrosion does not occur there.

Clearly, successful detection and resolution of the DC stray current interference problem depends on the degree of vigilance during annual surveillances and on prompt actions taken to mutually minimize corrosion risks, especially wherever the average positive potential variance is in excess of about 20 mV. Therefore, both the steel surface potential and the pH value of the protective film should be monitored and controlled to remain in the immunity range by effective cathodic protection. Also, as DC stray currents often are dynamic, and such exchanges tend to concentrate at points, the most practical means to solution should be accomplished proximate to that surface, where the alkalinity usually excludes the profitable use of galvanic anodes and impressed current may be considered infeasible. Certainly sacrificial anodes and grounding cells cannot galvanically corrode in the presence of corrosive solutions containing a high level of carbonates and/or in proximity to a steel interface provided with effective cathodic protection but impressed current can be utilized utilizing the cation exchange membrane technology (see, for example, U.S. Pat. No. 6,540,886). In addition, however, the response time of auto-potential controlled rectifiers to dynamic DC fluctuations often is too slow to maintain a potential variance that does not exceed 20 mV at the interface.

The embodiment illustrated in FIG. 4, including apparatus 10, could be used to mitigate or obviate the effects of DC stray current on the structure 64. Alternatively, the apparatus 10 could be used to locate a region of DC stray current. However, this embodiment may not necessarily provide the most timely response in terms of the impressing the necessary current density in response to pH and electrical potential measurements taken by the apparatus 10.

Figure 9:
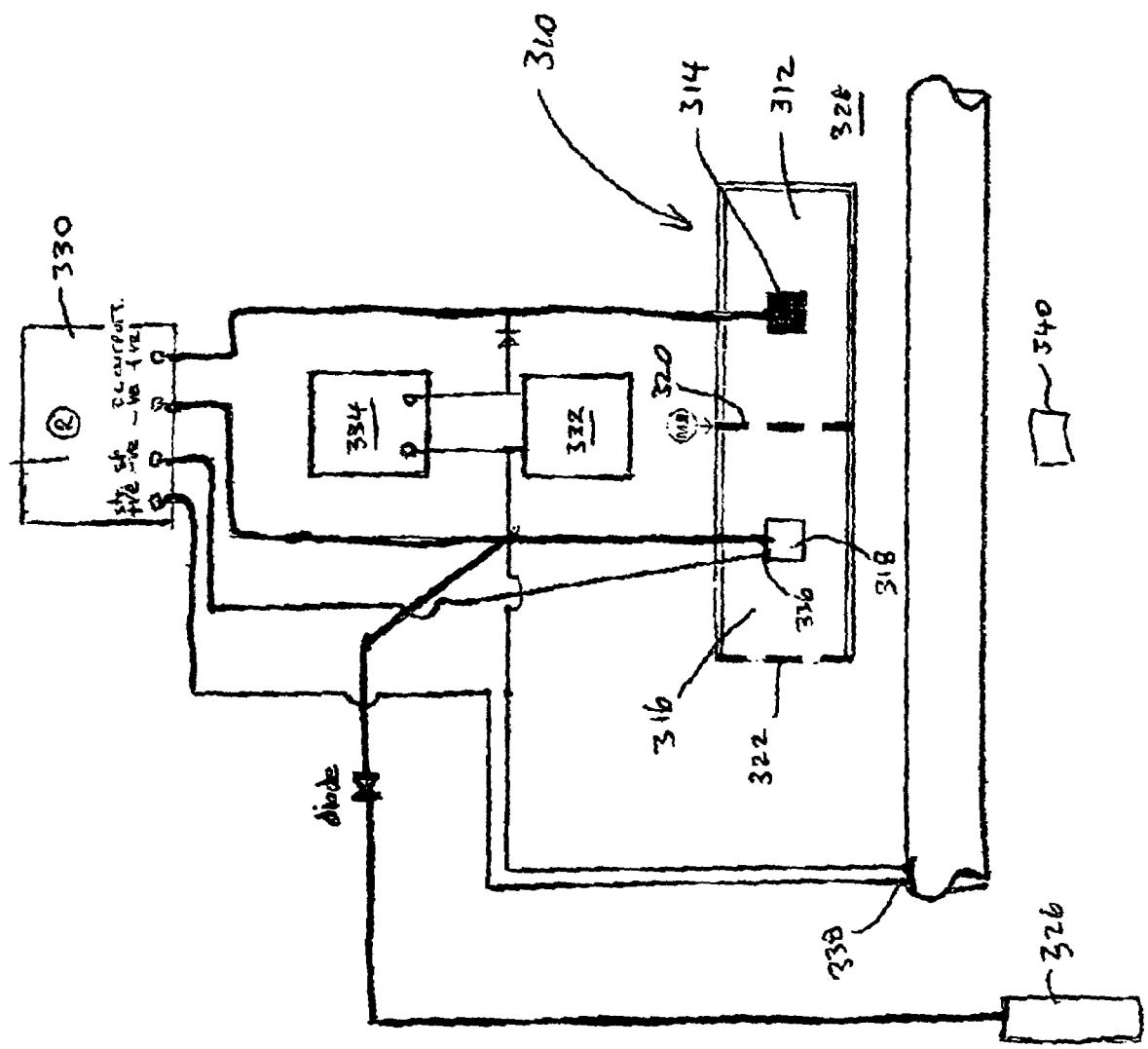
FIG. 9 is a schematic illustration of another embodiment of a system of the present invention.

In this respect, FIG. 9 provides a schematic illustration of a preferred embodiment of a system 300 of the present invention for mitigating or preventing the effects of DC stray current on the structure 64. A legend for the components of the system are provided as follows:

| Reference Numeral | Description |
| --- | --- |
| 310 | apparatus configured for travel through conduit 72 |
| 312 | anode compartment, containing KOH anolyte |
| 314 | anode |
| 316 | cathode compartment, containing NaOH catholyte |
| 318 | cathode |
| 320 | cation exchange membrane |
| 322 | porous bipolar membrane |
| 324 | high potential magnesium galvanic anode |
| 326 | cathodically polarized coated steel pipe |
| 328 | corrosive electrolyte |
| 330 | auto-potential controlled rectifier |
| 332 | battery |
| 334 | battery charger |
| 336 | reference electrode |
| 338 | reference electrode |
| 340 | foreign metallic structure |

The anode compartment 312 ionically communicates with the cathode compartment 316 through the cation exchange membrane 320.

The polarity of the reference electrodes 336, 338 switches depending on whether DC stray current is entering or being discharged from the pipeline 326.

The conduit 72 can be used to conveniently locate the apparatus 310 in a predetermined area of foreign current discharge or entry. The area of foreign current discharge or entry can be first predetermined, for example, by apparatus 10 being moved through the conduit 72. After positioning the apparatus 310 in the requisite area, the apparatus effects polarization of the area to effect reduction of the tendency for foreign sourced stray current to discharge to the environment 328, such as soil, or enter the pipeline 326 at this area.

The current impressed from the anode 314 in the anode compartment 312 maintains a high level of cathodic polarization capacitance at the large metallic surface of the cathode 318 in the cathode compartment 316. At the instant a DC stray current causes under-protection by discharging current from the surface of the pipeline 326, the capacitance stored in the protective film at the cathode 318 is instead harmlessly discharged. Alternatively, where the foreign DC stray current is imposing over-protection by entering the pipeline 326, the foreign DC stray current is replaced by protective current instantly discharged harmlessly from the cathode 318.

Where stray DC current interferences are significant, inevitably discharge points occur (often adjacent to foreign metallic structures) where the protective film is depleted or non existent or where corrosion occurs. The polarized potential in these areas may be in the order of −850 mV, −800 mV and more anodic that −700 mV (CSE), the corresponding pH values may be in the order of 10, 9 and less than 8 respectively to a pH of 4 or even more acidic. Potential is the best indicator of a problematic area but a decreasing pH value is a much more persuasive factor of the detrimental effects of DC stray current discharge, and values until well above 10 pH demark a quasi state of passivation from that of cathodically polarized corrosion prevention: thus pH values should be monitored carefully and utilized to control the current density required to maintain a target pH value of 10.5 up to about 12.5. Therefore the current density should be increased until the target pH value of 11.5 is maintained at a polarized potential that does not exceed about −1200 mV (CSE) (to avoid the over protection/danger zone). The problem with utilizing the polarized potential measurement to control impressed current output adjacent to stray DC current discharge areas is the delay in response as compared with the dynamic and probably more rapid changes of the current applied potential.

The entry of stray DC current at an area of the protected metal surface causes the surface polarized potential to shift negative at that location, however it is only feasible to shift the "true" (IR drop error free) polarized potential from about −550 mV (CSE) at a steel surface without protection to about −1200 mV (CSF) or perhaps a bit more, but that is the limitation to avoid creating a surplus of atomic and/or molecular hydrogen effervescing at the metal surface and promoting a serious stress to a protective coating as well as hydrogen embrittlement due to atomic hydrogen entry and combining with constituents to blister mild steels or crack hard steels.

A continuous net inflow of protective current at the stray DC current discharge area can maintain the polarized alkaline protective film thus reducing or obviating the corrosive effects at this area. By positioning capsule(s) adjacent to the discharge area, crevice pH and coupon potentials can be used to control current output through one or more impressed current anodes (sealed within an ion selective membrane to prevent over protection of the coated metal surface ). Each anode can be disposed adjacent to the discharge area but far enough from the capsule(s) to reduce their exposure to the impressed current gradient. Control of the impressed current output would be accomplished similar to that described above with respect to the manner by which cathodic protection of the structure 64 is controlled by the apparatus 10 except that polarized potentials would not be used by the programmable logic controller (PLC) in deciding to increase or decrease current output.

In a further embodiment, to protect public safety, for example, adjacent to an offshore pipeline structure, inaccessible except to professional divers, the impressed current anode source immersed in hydroxide is controlled at a safe current-applied potential to discharge through a series of compartments with membranes or a continuous pipe membrane inserted within the sensor conduit. The current is limited by the controller of the auto-potential controlled source sensing the potential measured at the reference electrodes proximate to the outside surface of the segmented or continuous membrane.

In another embodiment, the conduit 72 can be used for more efficiently effecting non-destructive testing ("NDT") indirect inspection techniques in relation to searching for and assessing holidays, coating deficiencies, and corrosion. Such NDT techniques include the Pearson Survey Technique (see "Contributions of J. M. Pearson NACE Publication 56-12), the Direct Current Voltage Gradient Technique (see http://dcrg.net), Electromagnetic Current Attenuation Survey, Alternating Current Voltage Gradient Survey, Close Order Potential Surveys, (see D. Kroon, K. W. Nicholas, J. B. Bushman, "Cathodic Protection Theory and Practice—The present Status", Conference Proceedings, 1982, I. Corr. S. I., and B. Husock, Corrosion 1961, 17, No. 8, 831), Scanning Electro Probe Techniques (see H. N. McMurray, G. Williams, S. O'Driscoll, and P. C. Morgan, "Scanning Electro Probe Techniques", Corrosion Management, November/December 2002), and Electrochemical Impedance Spectroscopy (see Guy D. Davis, Chester M. Dacres and Lorrie A. Krebs, "In-Situ Corrosion Sense for Coating Testing and Screening", Materials Performance, February 2000). Each of these techniques involve a transmission of radiation towards a target (such as the metal structure 64), and the receiving of a response of the target to the transmitted radiation, such response being indicative of a characteristic of the target. To facilitate NDT of the structure 64 by using conduit 72, the apparatus 10 is replaced by an apparatus 210 capable of transmitting radiation towards the structure 64 and receiving a response of the structure 64 to the transmitted radiation, such response being indicative of a characteristic of the target. The nature of the transmitted radiation (eg. sonic waves, electrical signal, radiowaves, electromagnetic waves, etc.) and the analysis of the response is dependent on the type of NDT technique used.

In this respect, another embodiment of the present invention provides a system 200 for effecting non-destructive testing of a characteristic of a target disposed in an aqueous electrolytic environment comprising means for effecting the non-destructive testing including a radiation transmitter for irradiating the target, and a receiver for receiving a response from the target to the radiation, and a passage for receiving movement of the receiver to effect positioning of the receiver at a predetermined location relative to the metal structure. As alluded to above, the target is a metal structure having a surface submerged in an aqueous electrolytic environment, such as an electrolytic soil environment.

An embodiment of this system 200 is illustrated in FIG. 8. The system 200 is similar to the system 62 illustrated in FIG. 4, with the primary exception that apparatus 10 is replaced with apparatus 210. The apparatus 210 includes a radiation transmitter for irradiating the structure 64, and a receiver for receiving a response from the structure 64 to the radiation. The apparatus 210 functions to perform non-destructive testing of the structure 64. In one embodiment, the apparatus 210 measures an indication of quality of coating or coating deficiencies applied to the structure 64 for purposes of mitigating corrosion of the structure 64. Indications of coating quality or coating deficiencies include the presence or absence of defects in the coating, such as holidays, coating disbondments, or other defects. The apparatus 210 can have an on-board power supply as well as an on-board means for recording and storing data collected by the receiver. The apparatus 210 can also transmit audio, visual, digital, or electronic signals to recording equipment 232 or an human operator.

Although the disclosure describes and illustrates preferred embodiments of the invention, it is to be understood that the invention is not limited to theses particular embodiments. Many variations and modifications will now occur to those skilled in the art. For definition of the invention, reference is to be made to the appended claims.

We claim:

1. A method of controlling cathodic protection being effected to a metal structure disposed in an electrolytic environment comprising:
   electrically connecting a metal coupon to the metal structure, wherein the metal coupon defines a simulated crevice;
   positioning the metal coupon at a predetermined position relative to the surface of the metal structure and within the electrolytic environment;
   applying a cathodic protection agent to the surface of the metal structure to effect cathodic protection of the surface of the metal structure;
   measuring a cathodic protection indication within the crevice;
   comparing the cathodic protection indication with a predetermined value; and
   adjusting the cathodic protection agent being applied to the metal structure in response to the comparison.

2. The method as claimed in claim 1, wherein the cathodic protection agent is an electric current.

3. The method as claimed in claim 1, wherein the cathodic protection agent is a chemical treatment agent.

4. The method as claimed in claim 3, wherein the chemical composition has a tendency to effect alkaline conditions at the metal structure.

5. The method as claimed in claim 1, wherein the predetermined position is in close proximity to the metal structure.

6. The method as claimed in claim 1, wherein the electrolytic environment is selected from the group consisting of: a subsurface soil environment and an aqueous solution.

7. The method as claimed in claimed 1, wherein the at least one cathodic protection indication includes pH and electric potential.

8. The method as claimed in claim 1, further comprising:
   measuring an electric potential proximate to the metal coupon and outside the crevice; and
   comparing the measured electric potential proximate to the metal coupon and outside the crevice with a respective predetermined value to provide a further comparison;
   wherein the step of adjusting the application of the cathodic protection agent is also in response to the further comparison.

9. The method as claimed in claim 1, wherein the metal coupon includes first and second opposing flanges joined by a web, such that the simulated crevice is defined by the space between the first and second flanges.

10. The method as claimed in claim 1, wherein the positioning of the metal coupon is effected by moving the metal coupon through a passage.

11. The method as claimed in claimed 1, wherein the at least two cathodic protection indications include pH and electric potential of the protective film measured in the crevice at the metal surface of the coupon.

12. The method as claimed in claim 11, further comprising:
   measuring an electric potential of the film proximate to the metal coupon and proximate to and outside the crevice; and
   comparing, automatically, the measured electric potential proximate to the metal coupon and outside the crevice with respective predetermined values to provide further comparisons;
   wherein the steps of adjusting, automatically, the application of the cathodic protection agent is also in response to the further comparisons.

13. A method of controlling cathodic protection being effected at the surface of a metal structure disposed in an electrolytic environment comprising:
   electrically connecting a metal coupon to the metal structure, wherein the metal coupon defines a simulated crevice;
   positioning the metal coupon at a predetermined position proximate to the surface of the metal structure and within the electrolytic environment;

applying a cathodic protection agent to the surface of the metal structure to effect cathodic protection of the surface of the metal structure;

measuring at least two cathodic protection indications within the crevice;

comparing each of the cathodic protection indications with a respective predetermined value; and adjusting, automatically, the cathodic protection agent being applied to the surface of the metal structure in response to each of the comparisons.

14. The method as claimed in claim 13, wherein the cathodic protection agent is a direct electric current.

15. The method as claimed in claim 14, wherein the cathodic protection agent is adjusted automatically by either increasing or decreasing protective current so that the polarized potential of the surface remains within the selected minimum and maximum limits in order to prevent corrosion of an iron or steel surface.

16. The method as claimed in claim 14, wherein the cathodic protection agent is adjusted automatically by the current applied potential sensed outside of the coupon crevice to maintain the potential between the selected predetermined minimum and maximum potential limitations.

17. The method as claimed in claim 14, wherein the cathodic protection agent is adjusted automatically by the polarized potential of the protective film sensed in the coupon crevice at the metal surface to maintain the selected minimum polarized potential limitations of about −900 mV (CSE) and maximum of about −1200 mV (CSE) in order to prevent corrosion of the iron or steel surface.

18. The method as claimed in claim 17, wherein the cathodic protection agent is further adjusted automatically by the pH sensed in the coupon crevice to increase the pH of the protective film produced at the metal surface sensed in the coupon crevice above 10 and maintain the pH between a minimum of about 11 to a maximum of about 12 in order to prevent corrosion of the iron or steel surface.

19. The method as claimed in any of claims 16, 17, or 18, wherein when the selected minimum or maximum potential and/or pH limitations of either indications are reached, all other indications are automatically overridden to limit further increases or decreases in protective current and an audible, visual or electronic alert is effected.

20. The method as claimed in claim 14, wherein the cathodic protection agent applied to iron or steel structures is adjusted hierarchically, by adjusting, initially, the current to satisfy the permissible range of potentials, thus overriding adjustments based on pH until the pH of the protective film is above pH 10. Then, either of these two indicators controls, automatically, the potential/pH equilibrium required for corrosion prevention of an iron or steel surface.

21. The method as claimed in claim 14, wherein the potential and pH criteria for each different metallic surface should be selected to match predetermined levels for automatic control of the cathodic protection agent for corrosion prevention as are known by those who are specialized in this art.

22. The method as claimed in claim 13, wherein the cathodic protection agent is an electrolyte.

23. The method as claimed in any of claims 14 and 22, wherein the direct current passing through the electrolyte has a tendency to effect polarization and alkalinity at the surface of the metal structure.

24. The method as claimed in claim 23, wherein the cathodic polarisation of the metal structure surface is improved by the addition of sodium and/or potassium hydroxides to the bulk electrolyte.

25. The method as claimed in claim 13, wherein the predetermined position is in close proximity to the metal structure, wherein the positioning of the metal coupon is effected by moving the metal coupon through a passage.

26. The method as claimed in claim 13, wherein the electrolytic environment is an aqueous solution selected from the group consisting of: a subsurface soil electrolyte, lakewater, seawater, or a process liquor.

27. The method as claimed in claim 13, wherein the cathodic protection indication includes pH of the polarized film measured in the crevice at the metal surface of the coupon.

28. The method as claimed in claim 13, wherein the cathodic protection indication includes electric potential of the polarized film measured in the crevice at the metal surface of the coupon.

29. The method as claimed in claim 13, wherein the metal coupon includes first and second opposing flanges joined by a web, such that the simulated crevice is defined by the space between the first and second flanges.

* * * * *